US009713461B2

(12) United States Patent
 Mikkaichi et al.

(10) Patent No.: US 9,713,461 B2
(45) Date of Patent: Jul. 25, 2017

(54) BODY FLUID COLLECTION DEVICE AND ENDOSCOPE SYSTEM

(71) Applicant: OLYMPUS CORPORATION, Tokyo (JP)

(72) Inventors: Takayasu Mikkaichi, Tokyo (JP); Satoko Kato, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/052,593

(22) Filed: Feb. 24, 2016

(65) Prior Publication Data

US 2016/0166239 A1 Jun. 16, 2016

Related U.S. Application Data

(63) Continuation of application No. PCT/JP2014/079833, filed on Nov. 11, 2014.

(30) Foreign Application Priority Data

Nov. 18, 2013 (JP) ................................. 2013-237903

(51) Int. Cl.
| | | |
|---|---|---|
| *A61M 1/00* | (2006.01) | |
| *A61B 1/00* | (2006.01) | |
| *A61B 1/12* | (2006.01) | |
| *A61B 10/00* | (2006.01) | |
| *A61B 10/02* | (2006.01) | |
| *A61B 10/04* | (2006.01) | |
| *A61B 1/015* | (2006.01) | |
| *A61B 1/018* | (2006.01) | |

(52) U.S. Cl.
CPC .......... *A61B 10/0045* (2013.01); *A61B 1/015* (2013.01); *A61B 1/018* (2013.01); *A61B 10/0283* (2013.01); *A61B 10/04* (2013.01)

(58) Field of Classification Search
CPC ............ A61B 1/00094; A61B 1/00119; A61B 1/00128; A61B 1/00137; A61B 1/015;
(Continued)

(56) References Cited

U.S. PATENT DOCUMENTS

2003/0042187 A1* 3/2003 Menne ................ A61M 1/0001
 210/136
2006/0287579 A1* 12/2006 Okada .................... A61B 1/012
 600/156
(Continued)

FOREIGN PATENT DOCUMENTS

JP S56-3045 A 1/1981
JP 2005-017280 A 1/2005
(Continued)

OTHER PUBLICATIONS

Jul. 14, 2015 Office Action issued in Japanese Patent Application No. 2015-522310.
(Continued)

*Primary Examiner* — Ryan Henderson
(74) *Attorney, Agent, or Firm* — Oliff PLC (57) ABSTRACT

A body fluid collection device comprises a longitudinal member having a lumen formed along a longitudinal axis and configured to be inserted through the channel, a flow path in which a suction is acted by the suction section of the endoscope, which is formed to bring the lumen of the longitudinal member in communication with the channel, an accommodating section which is formed in the flow path, and accumulate the the body fluid suctioned in the lumen by the suction section of the endoscope, and a sealing member configured to seal a space between the longitudinal member and the channel closer to a distal end of the longitudinal member than the suction port so that a fluid does not flow from the distal end side to a proximal end side of the longitudinal member.

7 Claims, 7 Drawing Sheets

(58) Field of Classification Search
CPC ........ A61B 1/12; A61B 1/125; A61M 1/0001; A61M 1/0003; A61M 1/0005; A61M 1/0007
USPC ................ 600/104, 106, 121–125, 153–159; 604/317, 319–321
See application file for complete search history.

(56) References Cited

U.S. PATENT DOCUMENTS

| | | | |
|---|---|---|---|
| 2008/0255424 A1* | 10/2008 | Durgin | A61B 1/0008 600/156 |
| 2009/0234192 A1 | 9/2009 | Okada | |
| 2011/0202015 A1 | 8/2011 | Park et al. | |

FOREIGN PATENT DOCUMENTS

| | | |
|---|---|---|
| JP | 2009-011419 A | 1/2009 |
| JP | 2009-527337 A | 7/2009 |
| JP | 2009-219858 A | 10/2009 |
| WO | 2006/030596 A1 | 3/2006 |
| WO | 2007/103057 A2 | 9/2007 |

OTHER PUBLICATIONS

Jan. 20, 2015 Search Report issued in International Patent Application No. PCT/JP2014/079833.

* cited by examiner

BODY FLUID COLLECTION DEVICE AND ENDOSCOPE SYSTEM

CROSS REFERENCE TO RELATED APPLICATIONS

This application is a continuation application based on a PCT Patent Application No. PCT/JP2014/079833, filed Nov. 1, 2014, whose priority is claimed on Japanese Patent Application No. 2013-237903, filed on Nov. 18, 2013, the entire content of which are hereby incorporated by reference.

BACKGROUND OF THE INVENTION

Field of the Invention

The present invention relates to a body fluid collection device used in combination with an endoscope having a suction section configured to suction the inside of a channel, and an endoscope system including the body fluid collection device and the endoscope.

Description of the Related Art

In the related art, body fluid collection devices are introduced into living bodies to collect body fluids and tests are performed on the living bodies using the body fluids. A known catheter is used for such collection of body fluids. When a body fluid such as duodenal juice or the like is collected using a catheter, a syringe is attached to a proximal end portion of the catheter. As a distal end portion of the catheter is endoscopically introduced into the duodenum and the inside of the catheter is suctioned by a syringe while the distal end portion of the catheter is in contact with the duodenal juice in the duodenum, the duodenal juice is suctioned into the catheter.

When duodenal juice is collected in this way, a user such as an operator or the like performs a general sequence of moving the distal end portion of the catheter while searching for a place appropriate for collection of the duodenal juice using the endoscope, and suctioning the duodenal juice when the place appropriate for the collection is found. For this reason, when the user is manipulating the syringe, the user cannot concentrate on finding the place appropriate for the collection using the endoscope.

Meanwhile, in order to easily and accurately collect a predetermined amount of blood, duodenal juice, or the like, a pipette disclosed in Japanese Unexamined Patent Application, First Publication No. 2005-17280 has been examined. The pipette has a first holder, parts of a suction port disposed in an attachment/guide section for the parts of the suction port of the first holder, a second holder engaged with the first holder, and a cap attached to the second holder.

A check valve configured to prevent a liquid from flowing from the first holder toward the parts of the suction port is provided between the parts of the suction port and the first holder. A temporary liquid suction body is attached to a temporary liquid suction body attachment section of the first holder.

A cap is formed of rubber or the like having flexibility and elasticity. A filter compression pin is inserted through a bottom section of the cap, and a through-hole having a slight gap around the filter compression pin is formed.

A method of using the pipette having the above-mentioned configuration is as follows.

A state in which distal ends of the parts of the suction port are dipped into blood or in contact with the blood is maintained. The first holder is pinched with one hand, and the cap is pressed with the other hand. Air in the cap is discharged to the outside via the gap of the cap, and the cap is dented. When the other hand is released, the cap returns to its original shape and the atmospheric pressure in the cap is decreased, and the blood is suctioned from the distal ends of the parts of the suction port. The blood arrives at the temporary liquid suction body through the check valve. The blood is suctioned into the temporary liquid suction body, and a color of the temporary liquid suction body changes.

SUMMARY

According to a first aspect of the present invention, A body fluid collection device configured to be used in combination with an endoscope having a channel and a suction section configured to suction the inside of the channel from a suction port in communication with the channel, the body fluid collection device comprises a longitudinal member having a lumen formed along a longitudinal axis and configured to be inserted through the channel, a flow path in which a suction is acted by the suction section of the endoscope, which is formed to bring the lumen of the longitudinal member in communication with the channel, an accommodating section which is formed in the flow path, and accumulate the body fluid suctioned in the lumen by the suction section of the endoscope, and a sealing member configured to seal a space between the longitudinal member and the channel closer to a distal end of the longitudinal member than the suction port so that a fluid does not flow from the distal end side to a proximal end side of the longitudinal member.

According to a second aspect of the present invention, the body fluid collection device in the first aspect may have a filter provided at the flow path and configured to allow passing of a gas and not to allow passing of a liquid.

According to a third aspect of the present invention, in the first aspect, the flow path may bring an opening of the proximal end side of the lumen in communication with an opening of the proximal end side of the channel.

According to a fourth aspect of the present invention, in the third aspect, a filter configured to allow passing of a gas and not to allow passing of a liquid may be provided at a hole formed in the flow path with no gap therebetween.

According to a fifth aspect of the present invention, in the third aspect, the accommodating section may have a first accommodating section and a second accommodating section being disposed in parallel in a direction crossing the longitudinal axis in the proximal end portion of the longitudinal member with respect to the opening of the proximal end portion of the lumen and partitioned by a wall section. The wall section sides of the first accommodating section and the second accommodating section may be opened, and the first accommodating section and the second accommodating section may be in communication with each other.

According to a sixth aspect of the present invention, in the fifth aspect, a discharge hole may be formed in the first accommodating section. A plug member detachably attached to the discharge hole and which is capable of sealing the discharge hole is provided.

According to a seventh aspect of the present invention, in the third aspect, a partition plate may be provided at the flow path. The accommodating section may be formed between the partition plate and an inner surface of the flow path. A first communication hole and a second communication hole penetrating in the plate thickness direction may be formed in the partition plate. The longitudinal member may be inserted through the second communication hole. The opening of the proximal end portion of the lumen may be disposed to be flush with a surface of the accommodating section side of the partition plate or disposed in the accommodating section.

According to an eighth aspect of the present invention, an endoscope system may comprise an endoscope having a channel and a suction section configured to suction the inside of the channel from a suction port in communication with the channel and the body fluid collection device according to the first aspect.

According to a ninth aspect of the present invention, an endoscope system may comprise an endoscope having a channel and a suction section configured to suction the inside of the channel from a suction port in communication with the channel and the body fluid collection device according to the second aspect.

According to a tenth aspect of the present invention, an endoscope system may comprise an endoscope having a channel and a suction section configured to suction the inside of the channel from a suction port in communication with the channel and the body fluid collection device according to the third aspect.

DETAILED DESCRIPTION OF THE PREFERRED EMBODIMENTS

First Embodiment

Hereinafter, a first embodiment of an endoscope system according to the present invention will be described with reference to FIGS. 1 to 3.

Figure 1:
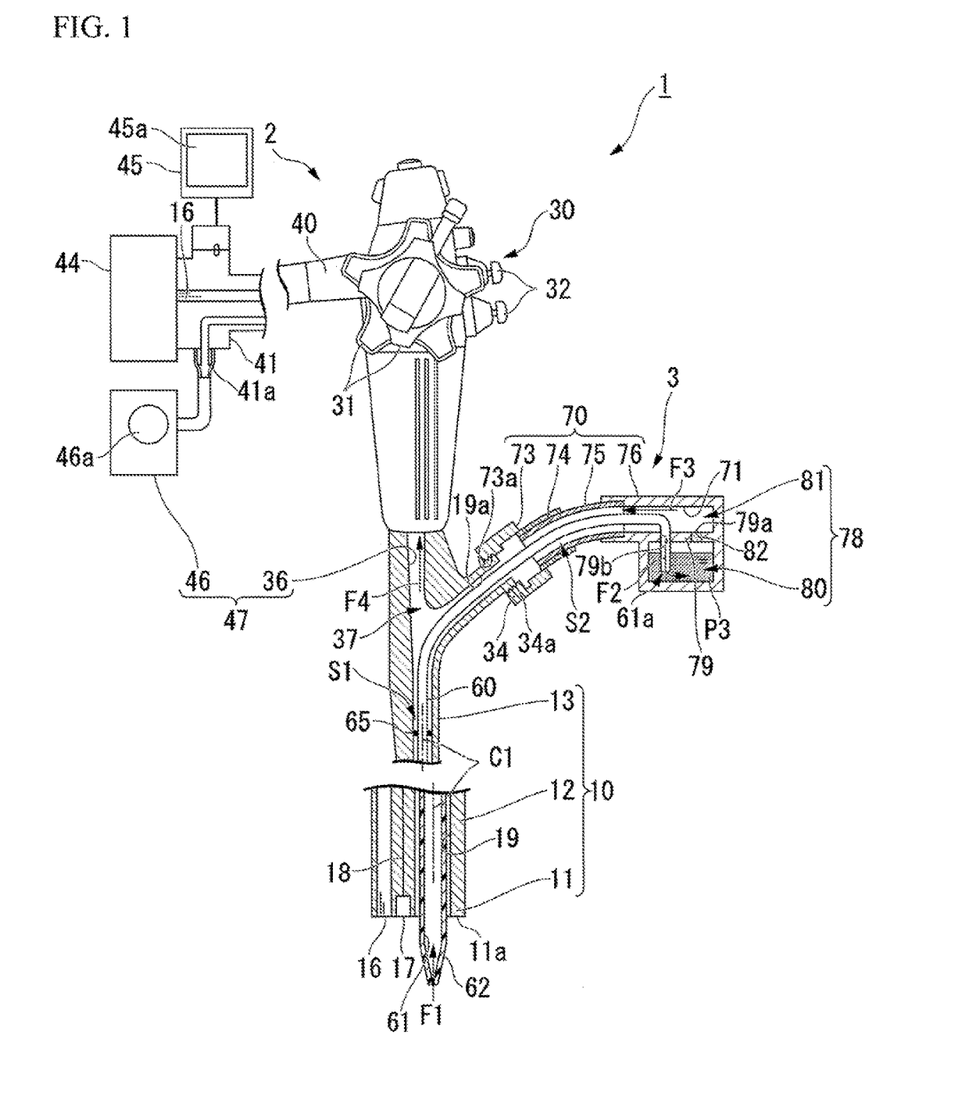
FIG. 1 is a general view in which a portion of an endoscope system of a first embodiment of the present invention is fractured.

As shown in FIG. 1, an endoscope system 1 of the present embodiment comprises an endoscope 2 having a channel (an insertion channel) 19, and a body fluid collection device (hereinafter, also referred to as "a device") 3 having a sheath (a major axis member) 60 that can be inserted into the channel 19. That is, the device 3 is used in combination with the endoscope 2.

The endoscope 2 is a so-called direct viewing type, and has an elongated insertion section 10, a manipulation unit 30 provided at a proximal end portion of the insertion section 10, and a universal cable 40 having one end portion attached to a side surface of the manipulation unit 30.

The insertion section 10 has a distal end rigid section 11 provided at a distal end, a curve section 12 attached to a proximal end portion of the distal end rigid section 11 and configured to be capable of being manipulated into a curve, and a flexible tube section 13 attached to a proximal end portion of the curve section 12 and has flexibility.

A light guide 16 consisted of a bundle of optical fibers and an observation unit 17 having an object lens and a charge coupled device (CCD) are provided at a distal end surface 11a of the distal end rigid section 11 and exposed to the outside.

The light guide 16 is inserted through the insertion section 10 and the manipulation unit 30 to extend to the universal cable 40. An object lens images an image of an observation target in front of the distal end rigid section 11 on a light receiving surface of the CCD. The CCD converts the image of the observation target into a signal that represents a picture, and transmits the converted signal to a signal wiring 18. The signal wiring 18 is inserted through the insertion section 10 and the manipulation unit 30 and extends to the universal cable 40.

An opening in communication with the above-mentioned channel 19 is formed in the distal end surface 11a of the distal end rigid section 11. A proximal end side of the channel 19 extends to the manipulation unit 30 through the flexible tube section 13.

In the curve section 12, while not shown, a plurality of curve pieces are connected in a longitudinal direction of the insertion section 10. A distal end portion of the manipulation wire is attached to the curve piece of the most distal end side. The proximal end side of the manipulation wire extends to the manipulation unit 30 through the flexible tube section 13.

A knob 31 configured to pull or push the manipulation wire or a switch 32 configured to manipulate an opening/closing valve or the like (not shown) provided in the manipulation unit 30 are provided at the manipulation unit 30. As the knob 31 is manipulated, the manipulation wire can be manipulated to curve the curve section 12 in a desired direction.

A forceps plug 34 in communication with the proximal end side of the channel 19 is provided at the distal end side of the manipulation unit 30. A male screw section 34a is formed at an outer circumferential surface of the forceps plug 34.

In the manipulation unit 30, a suction port 37 provided at a distal end portion of a suction tube path 36 is in communication with an intermediate section in a longitudinal direction of the channel 19. A proximal end side of the suction tube path 36 extends into the universal cable 40.

An integrated connector 41 is provided at the proximal end side of the universal cable 40. A light source device 44 and a monitor 45 are attached to the integrated connector 41.

The light source device 44 supplies illumination light emitted from a lamp (not shown) that is built therein to a proximal end surface of the light guide 16.

A signal processing circuit (not shown) is installed in the monitor 45. The signal transmitted through the signal wiring 18 is converted by the signal processing circuit, and the picture of the observation target acquired by the CCD is displayed on a display panel 45a of the monitor 45.

A suction device 46 is connected to a connector 41a provided at the integrated connector 41. A pump 46a configured to perform a suction operation is installed in the suction device 46. A suction section 47 is constituted by the suction device 46 and the above-mentioned suction tube path 36.

The suction device 46 connected to the connector 41*a* can suction the inside of the channel 19 through the suction tube path 36 and the suction port 37 by operating the pump 46*a* when the above-mentioned opening/closing valve is in an open state.

The device 3 has the above-mentioned sheath 60 having a lumen 61 formed along a longitudinal axis C1, an O-ring (a sealing member) 65 fixed to an outer circumferential surface of the sheath 60, and a reservoir (a communication section) 70 having a flow path 71 configured to bring an opening 61*a* of a proximal end portion of the lumen 61 in communication with an opening 19*a* of a proximal end portion of the channel 19.

The sheath 60 has a tapered section 62 formed at the distal end portion and having a diameter that reduces toward a distal end side. A length of the sheath 60 is larger than that of the channel 19. The sheath 60 is formed of a resin material such as polytetrafluoroethylene (PTFE) or the like to have a certain strength and flexibility such that the sheath 60 does not collapse even when the inside thereof is suctioned.

An outer diameter of the sheath 60 is smaller than an inner diameter of the channel 19. When the sheath 60 is inserted through the channel 19, a gap S1 is formed between an inner circumferential surface of the channel 19 and the sheath 60.

The O-ring 65 is formed of a material having elasticity such as rubber or the like. An outer diameter of the O-ring 65 is slightly larger than an inner diameter of the channel 19. The O-ring 65 is fixed to an outer circumferential surface of the sheath 60 by an adhesive agent or the like.

When the sheath 60 is inserted through the channel 19 of the endoscope 2 and the sheath 60 is protruded from the channel 19 to the distal end side, the O-ring 65 is configured to be positioned more distal than the suction port 37. That is, when the sheath 60 protrudes from the channel 19 to the distal end side, the O-ring 65 air-tightly seals a portion more distal than the suction port 37 between the sheath 60 and the channel 19. Further, airtightness disclosed herein also includes water-tightness.

The reservoir 70 has a connecting member 73 formed in a tubular shape and having a female screw section 73*a* threadedly engaged with the male screw section 34*a* of the forceps plug 34 and formed at an inner circumferential surface thereof, an outer tube 74 fixed to the proximal end side of the connecting member 73, an inner tube 75 slidably provided in the outer tube 74, and a reservoir main body 76 fixed to the proximal end side of the inner tube 75.

As a partition plate 79 is provided, a concave section 78 formed at the reservoir main body 76 has an accommodating section 80 serving as a closed space between the partition plate 79 and an inner surface of the concave section 78, and a connecting flow path 81 closer to an opening of the concave section 78 than the partition plate 79. That is, the concave section 78 is partitioned into the accommodating section 80 and the connecting flow path 81 by the partition plate 79.

A first communication hole 79*a* and a second communication hole 79*b* penetrating in the plate thickness direction are formed at the partition plate 79.

A scale (an indicator) configured to measure an amount of duodenal juice P3 accommodated in the accommodating section 80 (to be described below) may be provided at the accommodating section 80.

A filter 82 configured to allow penetration of a gas and not to allow penetration of a liquid is disposed in the first communication hole 79*a*. The filter 82 is provided with no gap with the inner circumferential surface of the first communication hole 79*a*.

For example, Gore-Tex (registered trademark, produced by WL Gore & Associates, Inc.) or the like may be appropriately used as the filter 82.

The connecting member 73, the outer tube 74, the inner tube 75 and the reservoir main body 76 may be formed of a known resin material. The connecting member 73 and other members may be formed of a transparent resin material so that the inside can be easily checked.

The connecting member 73 and the outer tube 74 are fixed in an air-tight connection. In addition, the inner tube 75 and the reservoir main body 76 are fixed in an air-tight connection. A sealing section such as an O-ring or the like (not shown) is provided between the outer tube 74 and the inner tube 75, the outer tube 74 and the inner tube 75 are air-tightly connected, and the inner tube 75 can be slid with respect to the outer tube 74 while being air-tightly held.

The above-mentioned flow path 71 is consisted of a tubular hole of the connecting member 73, tubular holes of the outer tube 74 and the inner tube 75, and the concave section 78 of the reservoir main body 76. The above-mentioned filter 82 is provided with no gap with the inner circumferential surface of the flow path 71 configured to bring the opening 61*a* of the proximal end portion of the lumen 61 in communication with the opening 19*a* of the proximal end portion of the channel 19. That is, a fluid flowing through the flow path 71 always passes through the filter 82.

An inner diameter of the tubular hole of the connecting member 73 and an inner diameter of the tubular hole of the inner tube 75 are larger than the outer diameter of the sheath 60, and a gap S2 is formed between the inner circumferential surface of the tubular hole of the connecting member 73, the inner circumferential surface of the tubular hole of the inner tube 75 and the sheath 60.

The proximal end portion of the sheath 60 is inserted through the second communication hole 79*b* from the connecting flow path 81 side. The opening 61*a* of the proximal end portion of the lumen 61 is disposed in the accommodating section 80 with no contact with the inner wall surface of the accommodating section 80. The inner circumferential surface of the second communication hole 79*b* and the sheath 60 are air-tightly sealed.

The sheath 60 of the device 3 is inserted through the channel 19 of the endoscope 2, and the female screw section 73*a* of the connecting member 73 is threadedly engaged with the male screw section 34*a* of the forceps plug 34. The forceps plug 34 and the connecting member 73 are air-tightly connected to each other, and a portion closer to the proximal end side than the O-ring 65 in the lumen 61 and a portion closer to the proximal end side than the O-ring 65 in the channel 19 come in communication with each other via the filter 82 through the reservoir 70.

Next, an action when the endoscope system 1 having the above-mentioned configuration is used will be described with reference to the case in which duodenal juice is collected as a body fluid. Further, the duodenal juice disclosed herein includes not only duodenal juice referring in a narrow sense to that secreted from the duodenum but also pancreatic juice and bile.

Figure 2:
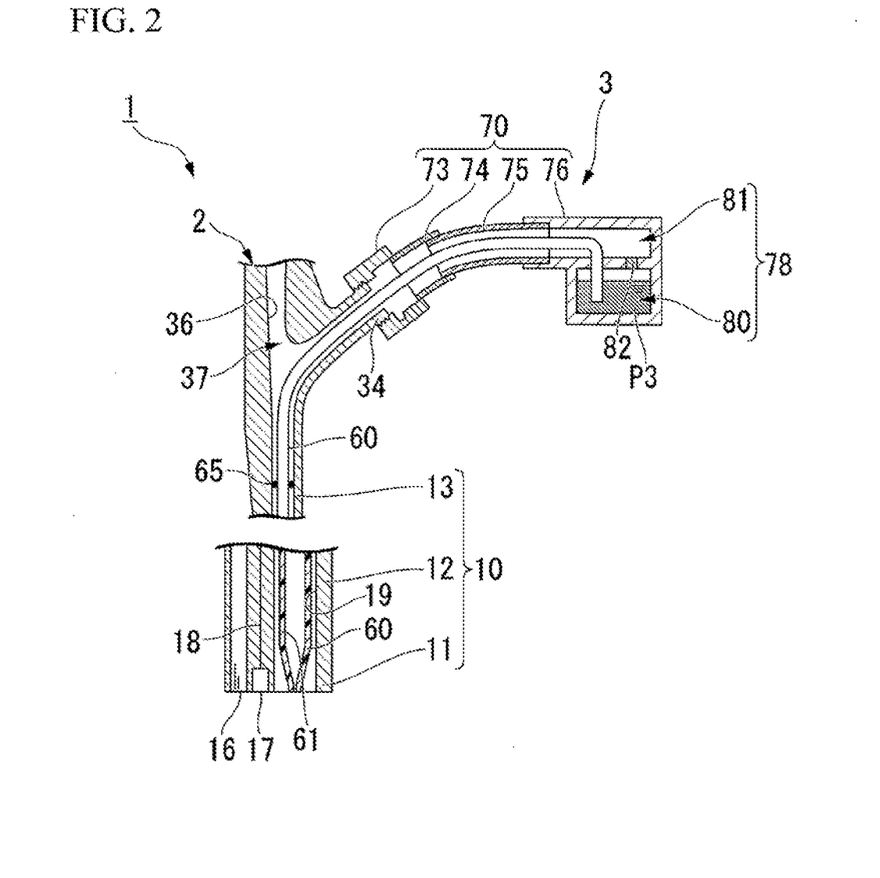
FIG. 2 is a cross-sectional view showing a sequence of collecting duodenal juice using the endoscope system.
Figure 3:
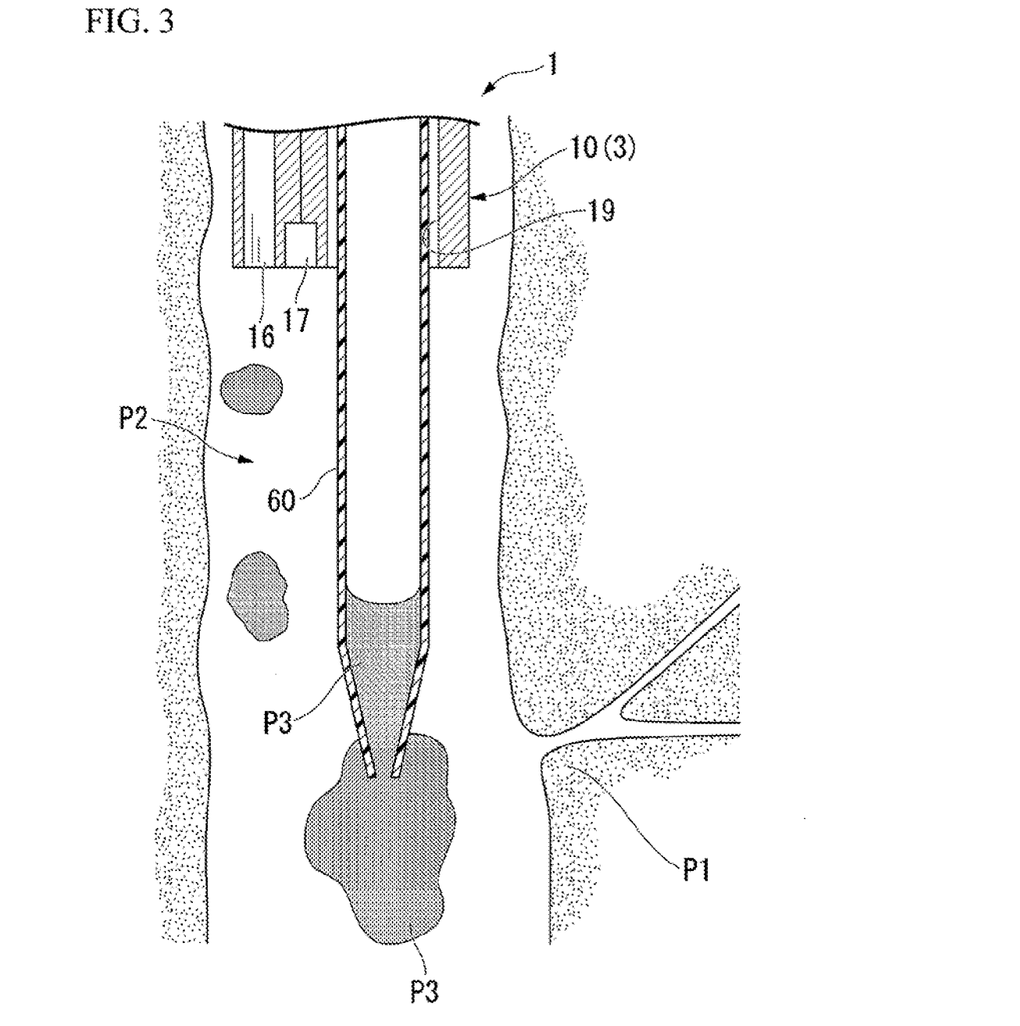
FIG. 3 is a cross-sectional view showing the sequence of collecting the duodenal juice using the endoscope system.

First, a user such as an operator or the like brings back the reservoir main body 76 and the sheath 60 by moving (pulling back) the inner tube 75 to the proximal end side with respect to the outer tube 74 outside the body of the patient as shown in FIG. 2, and accommodates the distal end portion of the sheath 60 in the channel 19.

The illumination light emitted from the light source device 44 is radiated to the front of the insertion section 10 via the light guide 16. The insertion section 10 of the endoscope 2 is inserted into the body of the patient from a natural opening such as the mouth or the like, and as shown in FIG. 3, the insertion section 10 moves forward to the duodenum P2 in the vicinity of the duodenal papilla P1.

When the insertion section 10 is inserted, the knob 31 is manipulated to appropriately curve the curve section 12 according to necessity while observing the picture displayed on the display panel 45a of the monitor 45.

The inner tube 75 is moved (pushed) to the distal end side with respect to the outer tube 74, and the distal end portion of the sheath 60 protrudes from the channel 19. The reservoir 70 is maintained so that the accommodating section 80 is disposed below with respect to the opening 61a of the lumen 61 (see FIG. 1).

A user finds a place appropriate for collection of the duodenal juice P3 while inserting the sheath 60 through the duodenum P2, manipulating the knob 31 to appropriately curve the curve section 12 or moving the sheath 60 forward and backward or rotating it by manipulating the proximal end side of the sheath 60.

When the appropriate place is found, the switch 32 is manipulated to operate the suction device 46, and the inside of the channel 19 is suctioned. As the O-ring 65 is provided between the sheath 60 and the channel 19, the duodenal juice P3 or a gas (not shown) in the duodenum P2 are suctioned as shown by an arrow F1 from the distal end portion of the lumen 61 as shown in FIG. 1, and enters the accommodating section 80 as shown by an arrow F2 from the opening 61a of the proximal end portion of the lumen 61. Since the filter 82 allows penetration of the gas, the gas flows outside the sheath 60 and in the connecting flow path 81 through the filter 82 as shown by an arrow F3. Since the portion closer to the distal end side than the suction port 37 between the sheath 60 and the channel 19 is sealed by the O-ring 65, the gas flows through the suction tube path 36 from the suction port 37 to be exhausted to the outside as shown by an arrow F4.

Meanwhile, since the filter 82 does not allow penetration of the liquid, the duodenal juice P3 stays in the accommodating section 80 without passing through the filter 82. A user manipulates the switch 32 and stops the suction device 46 when a certain amount of duodenal juice P3 is collected in the accommodating section 80 with reference to the scale of the accommodating section 80 while checking the inside of the accommodating section 80. The certain amount disclosed herein is, for example, 50 µl (microliters).

The inner tube 75 is brought back to accommodate the distal end portion of the sheath 60 in the channel 19. The sheath 60 of the device 3 is pulled out of the mouth of the patient together with the insertion section 10 of the endoscope 2.

As the screw fitting is removed, the connecting member 73 is removed from the forceps plug 34 and the sheath 60 is extracted from the channel 19.

After the accommodating section 80 of the reservoir main body 76 is broken or the like, the duodenal juice P3 in the accommodating section 80 is added to a diluted solution. The concentration of a specific tumor marker in the pancreatic juice in the diluted solution is measured, and a test for pancreatic cancer or the like is performed.

As described above, according to the device 3 and the endoscope system 1 of the present embodiment, when the suction section 47 is operated to be suctioned from the suction port 37, a space between the sheath 60 and the channel 19 is sealed by the O-ring 65, and since the lumen 61 and the channel 19 are in communication with each other through the reservoir 70, the fluid in the lumen 61 is suctioned. The duodenal juice P3 suctioned from the distal end of the sheath 60 stays in the accommodating section 80 of the reservoir 70. Accordingly, the duodenal juice P3 can be automatically and continuously suctioned into the accommodating section 80 from the distal end portion of the lumen 61 through the lumen 61 using the suction section 47 provided on the endoscope 2 of the related art.

Since suction of the duodenal juice P3 can be automatically performed, a user can concentrate on finding the place appropriate for collection of the duodenal juice P3 using the endoscope 2.

Since the suction can be performed by manipulating the switch 32 provided in the manipulation unit 30, the duodenal juice P3 can be efficiently suctioned even when the duodenal juice P3 is scattered.

In addition, as the filter 82 is provided at the flow path 71, separation of the gas and the duodenal juice P3 can be easily and securely performed.

Second Embodiment

Next, while a second embodiment of the present invention will be described with reference to FIG. 4, parts that are the same as those of the previous embodiment are designated by the same reference numerals, a description thereof will be omitted and only different points will be described.

Figure 4:
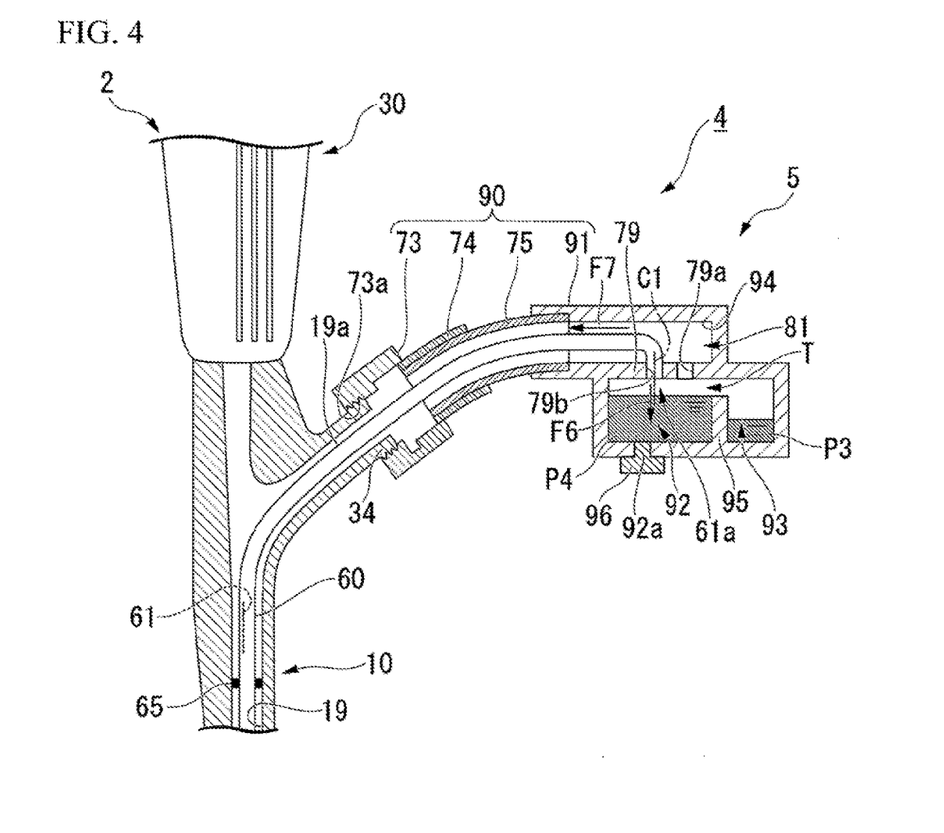
FIG. 4 is a view of a major part in which a portion of an endoscope system of a second embodiment of the present invention is fractured.

As shown in FIG. 4, a device 5 of an endoscope system 4 of the present embodiment comprises a reservoir 90 instead of the reservoir 70 of the device 3 of the first embodiment. A reservoir main body 91 of the reservoir 90 has a first accommodating section 92 and a second accommodating section 93 instead of the accommodating section 80, without having the filter 82 with respect to the reservoir main body 76.

The first accommodating section 92 and the second accommodating section 93 are formed in a flow path 94 of the reservoir 90. The first accommodating section 92 and the second accommodating section 93 are disposed parallel to a direction crossing the longitudinal axis C1 at the proximal end portion of the lumen 61 with respect to the opening 61a of the proximal end portion of the lumen 61. The first accommodating section 92 and the second accommodating section 93 are partitioned by a wall section 95, and both sides of the wall section 95 are opened. Accordingly, a communication space T configured to bring the first accommodating section 92 and the second accommodating section 93 in communication with each other is formed in the wall section 95. Accordingly, the first accommodating section 92 and the second accommodating section 93 are disposed with the connecting space T sandwiched therebetween.

The first accommodating section 92 is disposed to oppose the opening 61a of the lumen 61. In this example, the proximal end of the lumen 61 is flush with a surface of the connecting space T side of the partition plate 79.

A discharge hole 92a arriving at the outer surface of the reservoir main body 91 is formed at the bottom surface opposite to the connecting space T in the first accommodating section 92. A plug member 96 is detachably attached to the discharge hole 92a. The plug member 96 is formed of a material having elasticity such as rubber or the like. The plug member 96 can seal the discharge hole 92a when attached to the discharge hole 92a.

The reservoir main body 91 may be formed of a transparent resin material like the reservoir main body 76.

When the endoscope system 4 having the above-mentioned configuration is used, the reservoir 90 is maintained so that the first accommodating section 92 is disposed below with respect to the opening 61a of the lumen 61.

When the place appropriate for collection of the duodenal juice P3 is found, the suction device 46 is operated. The duodenal juice P3 or the gas is suctioned from the lumen 61 as shown by an arrow F6, and the duodenal juice P3 stays in the first accommodating section 92 under its own weight. Meanwhile, the gas flows from the lumen 61 through the connecting space T and the first communication hole 79a as shown by an arrow F7 to be discharged to the outside.

When the suction device 46 is operated, the amount of the duodenal juice P3 staying in the first accommodating section 92 gradually increases, and when a certain amount of the duodenal juice P3 is collected in the first accommodating section 92, the duodenal juice P3 supplied from the lumen 61 flows into the second accommodating section 93 from the first accommodating section 92 through the connecting space T over the wall section 95.

A user checks the inside of the accommodating sections 92 and 93, and manipulates the switch 32 to stop the suction device 46 after checking that the duodenal juice P3 flows into the second accommodating section 93.

After a container (not shown) is disposed under the discharge hole 92a, the plug member 96 is removed from the discharge hole 92a. The duodenal juice P3 staying in the first accommodating section 92 flows below the discharge hole 92a through the discharge hole 92a and stays in the container.

In this way, the certain amount of the duodenal juice P3 is collected in the container.

When the duodenal juice P3 is collected several times, the first accommodating section 92 is maintained so that an inclination of the first accommodating section 92 with respect to a vertical direction is constant.

As described above, according to the device 5 and the endoscope system 4 of the present embodiment, since the duodenal juice P3 is automatically and continuously suctioned, a user can concentrate on finding the place appropriate for collection of the duodenal juice P3 using the endoscope 2.

Since the accommodating sections 92 and 93 are formed at the reservoir 90, as the suction section 47 is operated in a state in which the reservoir 90 is maintained so that the first accommodating section 92 is disposed below with respect to the opening 61a of the lumen 61, the duodenal juice P3 can stay in the first accommodating section 92. As the suction section 47 is stopped when the duodenal juice P3 flows into the second accommodating section 93 from the first accommodating section 92 through the connecting space T over the wall section 95, the certain amount of the duodenal juice P3 can be collected in the first accommodating section 92.

As the plug member 96 is removed from the discharge hole 92a, the duodenal juice P3 staying in the first accommodating section 92 can be easily discharged to the outside of the reservoir 90 and collected.

Third Embodiment

Next, while a third embodiment of the present invention will be described with reference to FIGS. 5 to 7, parts that are the same as those of the previous embodiments are designated by the same reference numerals, a description thereof will be omitted and only different points will be described.

Figure 5:
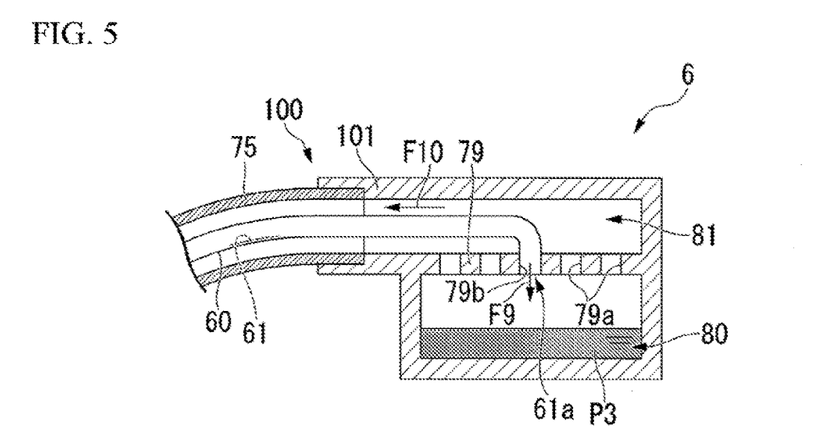
FIG. 5 is a cross-sectional view of a major part of a body fluid collection device of a third embodiment of the present invention.
Figure 6:
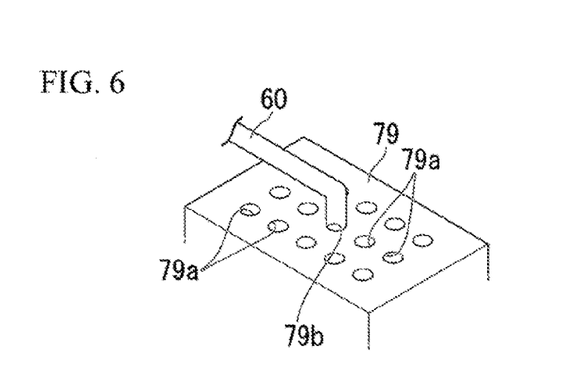
FIG. 6 is a perspective view of a sheath and a partition plate of the body fluid collection device.

As shown in FIG. 5, a device 6 of the present embodiment includes a reservoir 100 instead of the reservoir 70 of the device 3 of the first embodiment. A reservoir main body 101 of the reservoir 100 has one second communication hole 79b and a plurality of first communication holes 79a formed at the partition plate 79 as shown in FIGS. 5 and 6, without the filter 82 being provided in the reservoir main body 76.

In this example, the plurality of first communication holes 79a are formed in the partition plate 79 in a lattice shape, and the second communication hole 79b is formed in a central portion of the partition plate 79. Inner surfaces of the plurality of first communication holes 79a may be small as long as the gas can pass therethrough.

The opening 61a of the proximal end portion of the lumen 61 is disposed to oppose the accommodating section 80. A volume in the accommodating section 80 is a certain volume to which the duodenal juice P3 is to be collected.

A suction force by the pump 46a of the suction device 46 is set to be smaller than that of the first embodiment.

When the device 6 having the above-mentioned configuration is used with the endoscope 2, the reservoir 90 is maintained so that the accommodating section 80 is disposed below with respect to the opening 61a of the lumen 61.

When the place appropriate for collection of the duodenal juice P3 is found, the suction device 46 is operated. The duodenal juice P3 or the gas is suctioned from the lumen 61 as shown by an arrow F9 shown in FIG. 5, and the duodenal juice P3 stays in the accommodating section 80 due to the gravity applied thereto. Meanwhile, the gas flows from the lumen 61 through above the duodenal juice P3 accommodated in the accommodating section 80 and the first communication hole 79a to be discharged to the outside as shown by an arrow F10.

Figure 7:
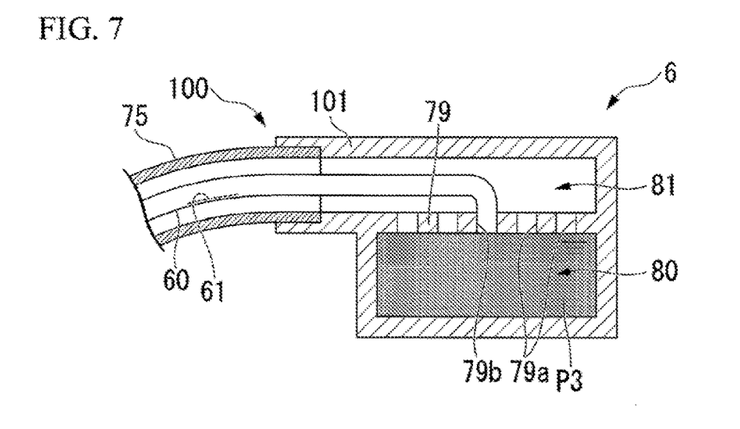
FIG. 7 is a cross-sectional view showing a sequence of collecting duodenal juice using the body fluid collection device.

When the inside of the accommodating section 80 is filled with the duodenal juice P3 as shown in FIG. 7, since the gas cannot flow over the duodenal juice P3, the duodenal juice P3 or the gas cannot be suctioned.

In this way, the certain amount of the duodenal juice P3 is collected in the accommodating section 80.

As described above, according to the device 6 of the present embodiment, since the duodenal juice P3 is automatically and continuously suctioned, the user can concentrate on finding the place appropriate for collection of the duodenal juice P3 using the endoscope 2.

Further, in the present embodiment, while the plurality of first communication holes 79a are formed in the partition plate 79, the number of the first communication holes 79a formed in the partition plate 79 may be one.

Fourth Embodiment

Next, while a fourth embodiment of the present invention will be described with reference to FIG. 8, the parts that are the same as those of the previous embodiments are designated by the same reference numerals, a description thereof will be omitted and only different points will be described.

Figure 8:
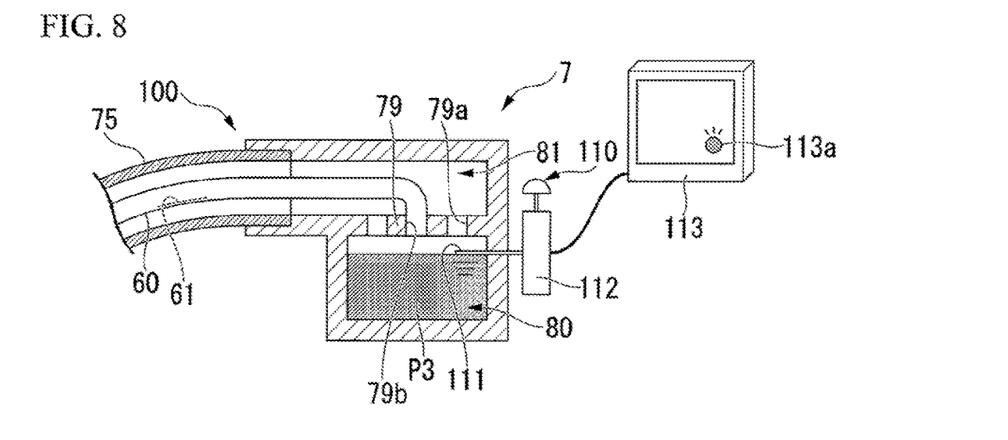
FIG. 8 is a view of a major part in which a portion of a body fluid collection device of a fourth embodiment of the present invention is fractured.

As shown in FIG. 8, a device 7 of the embodiment includes a liquid amount measurement device 110 configured to detect a liquid surface in the accommodating section 80, in addition to the components of the device 6 of the third embodiment.

The liquid amount measurement device 110 can use the known configuration, and a sensor unit 111 of the liquid amount measurement device 110 is disposed in the accommodating section 80. A measurement device main body 112 of the liquid amount measurement device 110 detects that the sensor unit 111 comes in contact with the duodenal juice P3, and the measurement device main body 112 displays a warning mark 113a on, for example, a monitor 113 based on the detected result.

The user who checks the displayed warning mark 113a manipulates the switch 32 to stop the suction device 46.

According to the device 7 of the embodiment having the above-mentioned configuration, the certain amount of the duodenal juice P3 can be securely collected.

Fifth Embodiment

Next, while a fifth embodiment of the present invention will be described with reference to FIGS. 9 and 10, the parts that are the same as those of the previous embodiments are designated by the same reference numerals, a description thereof will be omitted and only different points will be described.

Figure 9:
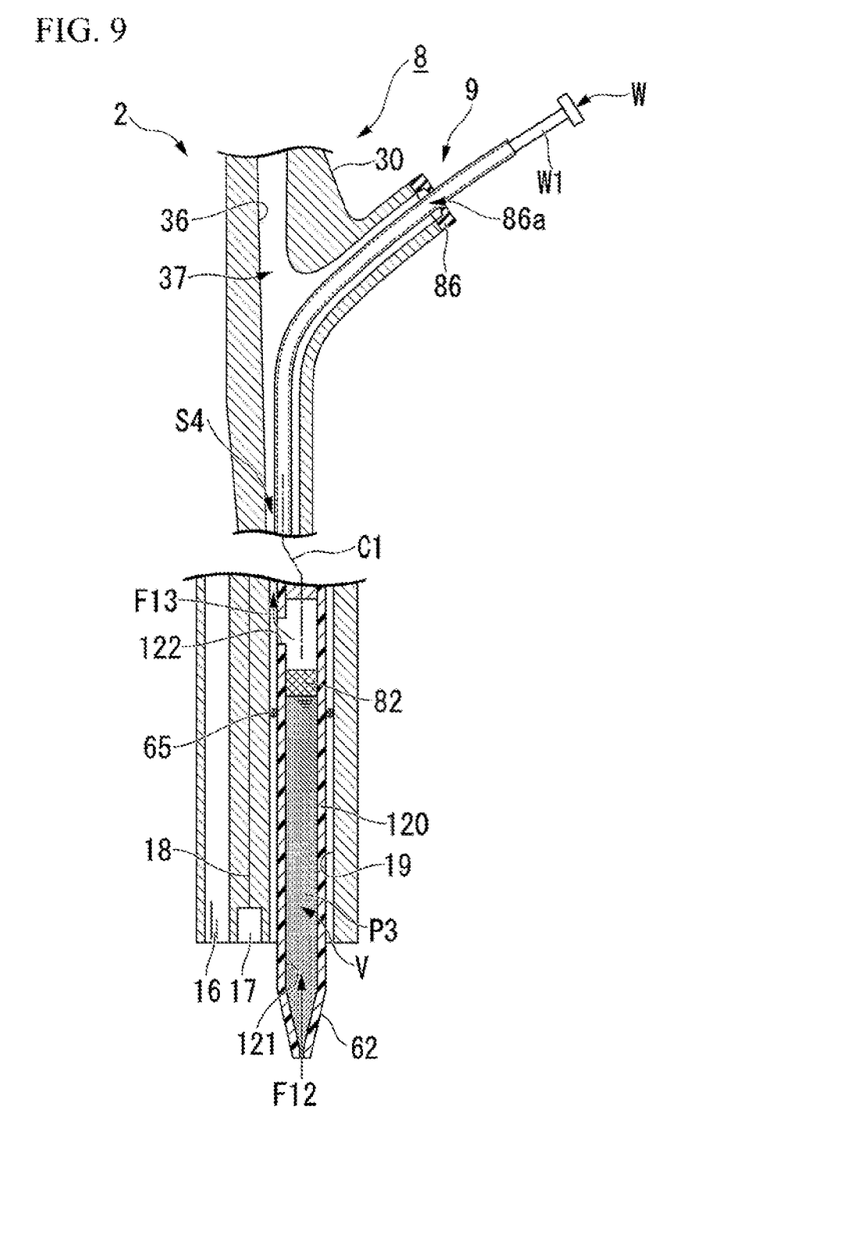
FIG. 9 is a cross-sectional view of a major part of an endoscope system of a fifth embodiment of the present invention.

As shown in FIG. 9, an endoscope system 8 of the present embodiment includes the above-mentioned endoscope 2, and a device 9 having a sheath 120 that can be inserted through the channel 19 of the endoscope 2.

A forceps plug 86 of the endoscope 2 can air-tightly seal the proximal end portion of the channel 19 when the sheath 120 is not inserted through a through-hole 86a and when the sheath 120 is inserted therethrough.

The sheath 120 may be formed in the same shape as the above-mentioned sheath 60. The above-mentioned O-ring 65 is fixed to the outer circumferential surface of the sheath 120. When the sheath 120 is inserted through the channel 19 of the endoscope 2 and the sheath 120 protrudes from the channel 19 toward the distal end side, the O-ring 65 is disposed closer to the distal end side than the suction port 37. That is, when the sheath 120 protrudes from the channel 19 toward the distal end side, the O-ring 65 air-tightly seals the portion closer to the distal end side than the suction port 37 between the sheath 120 and the channel 19.

A side hole (a communication section) 122 formed to arrive at a lumen 121 of the sheath 120 from the outer circumferential surface of the portion closer to the proximal end side than the O-ring 65 in the sheath 120 is formed at the sheath 120. That is, a hole configured to bring the channel 19 closer to the proximal end side than the O-ring 65 in communication with the lumen 121 closer to the proximal end side than the filter 82 is formed in the sheath 120. The hole 122 is a hole configured to bring a portion closer to the proximal end side than the O-ring 65 in the lumen 121 in communication with a portion closer to the proximal end side than the O-ring 65 in the channel 19.

The above-mentioned filter 82 is provided at the portion closer to the distal end side than the side hole 122 in the lumen 121. A collection volume V is defined by the portion closer to the distal end side than the filter 82 in the lumen 121. The size of the collection volume V is equal to a volume of the certain amount of the duodenal juice P3 to be collected.

In this example, a known stylet W is inserted through the lumen 121 of the sheath 120 from the proximal end side of the lumen 121. An outer diameter of a rod-shaped main body W1 provided at the distal end side of the stylet W is slightly smaller than an inner diameter of the lumen 121. A distal end of the main body W1 is disposed closer to the proximal end side than the side hole 122.

An action when the endoscope system 8 having the above-mentioned configuration is used will be described in the case in which the duodenal juice P3 is collected as the body fluid.

First, a user moves the insertion section 10 of the endoscope 2 forward to the duodenum P2 in the vicinity of the duodenal papilla P1 through the mouth and maintains the insertion section 10 at the position. The sheath 120 is inserted into the channel 19 through the forceps plug 86 of the endoscope 2, and the distal end portion of the sheath 120 protrudes from the channel 19.

The user inserts the sheath 120 into the duodenum P2, and looks for the place appropriate for collection of the duodenal juice P3 while manipulating the knob 31.

Upon finding the appropriate place, the user manipulates the switch 32 to operate the suction device 46, and the inside of the channel 19 is suctioned. While not shown in detail, the duodenal juice P3 or the gas in the duodenum P2 is suctioned from the distal end portion of the lumen 121 as shown in FIG. 9 by an arrow F12. Since the gas passes through the filter 82 and the portion closer to the proximal end side than the side hole 122 in the lumen 121 is sealed by the main body W1 of the stylet W, the gas passes through the filter 82 and the side hole 122, flows through a gap S4 between the inner circumferential surface of the channel 19 and the sheath 120 as shown by an arrow F13, and flows through the suction tube path 36 to be exhausted to the outside.

Meanwhile, since the filter 82 does not allow penetration of a liquid, the duodenal juice P3 stays in the collection volume V without passing through the filter 82. When the inside of the collection volume V is filled with the duodenal juice P3, the duodenal juice P3 cannot be suctioned.

Figure 10:
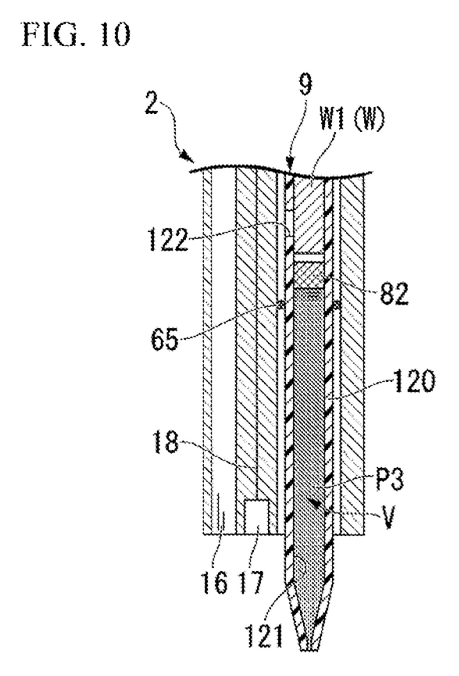
FIG. 10 is a cross-sectional view of a major part showing a sequence of collecting duodenal juice using the endoscope system.

A user presses the stylet W against the sheath 120 as shown in FIG. 10, and seals the side hole 122 of the sheath 120 with the distal end side of the main body W1. While the switch 32 is manipulated to stop the suction device 46, since air or the like does not passes through the side hole 122 and the filter 82 to flow through the collection volume V, the duodenal juice P3 in the collection volume V does not flow to the outside from the distal end of the lumen 121.

The sheath 120 is pulled out of the forceps plug 86 together with the stylet W.

After a container (not shown) is disposed under the distal end of the sheath 120, the stylet W is brought back with respect to the sheath 120 and sealing of the side hole 122 is released. The air flows into the collection volume V through the side hole 122 and the filter 82, and the duodenal juice P3 flowing out of the distal end of the lumen 121 stays in the container.

In this way, the certain amount of the duodenal juice P3 is collected in the container.

As described above, according to the device 9 and the endoscope system 8 of the present embodiment, since the duodenal juice P3 is automatically and continuously suctioned, the user can concentrate on finding the place appropriate for collection of the duodenal juice P3 using the endoscope 2.

Since the communication section is the side hole 122 of the sheath 120, the device 9 can be configured simply.

Since the filter 82 is provided at the lumen 121, the certain amount of the duodenal juice P3 corresponding to the collection volume V can be easily collected.

Further, in the present embodiment, a sealing plug formed of a material having elasticity such as rubber or the like may be provided at the distal end of the main body W1 of the stylet W, and the side hole 122 may be sealed by the sealing plug. In this case, the outer diameter of the main body W1 may be sufficiently smaller than the inner diameter of the lumen 121.

Hereinabove, the first to fifth embodiments of the present invention have been described in detail with reference to the accompanying drawings, but specific configurations are not limited to these embodiments and may include modifications, combinations, or the like of the configurations without departing from the spirit of the present invention. Further, it is needless to say that the configurations shown in the embodiments may be appropriately combined.

For example, in the first embodiment to the fifth embodiment, the sealing member is the O-ring 65. However, the sealing member is not limited thereto but may be a check valve configured to seal a space between the sheath and the channel 19 of the endoscope 2 to prevent fluids such as air or the like from flowing from the distal end side toward the proximal end side.

In the embodiment, while the duodenal juice P3 is collected as the body fluid, the body fluid is not limited thereto but, for example, bile, pancreatic juice, or the like may be collected.

The forceps plug and the connecting member 73 are air-tightly connected by screw fitting. However, the connection between the forceps plug and the connecting member 73 is not limited thereto as long as they can be air-tightly connected but, for example, a known Luer lock structure may be applied.

While the case in which the device is used in combination with the direct viewing type endoscope 2 has been described, the device may be used in combination with a so-called lateral vision type endoscope.

All of the components described in the above-mentioned embodiments may be implemented in appropriate combinations or omitted within the technical spirit of the present invention.

Further, while preferred embodiments of the present invention have been described, the present invention is not limited to the embodiments. Additions, omissions, substitutions and other modifications of the components may be made without departing from the spirit of the present invention. The present invention is not limited to the above-mentioned description and is limited only by the accompanying claims.

The invention claimed is:

1. A body fluid collection device configured to be used in combination with an endo scope having an insertion section configured to be inserted into a body of a patient, an insertion channel configured to be communicated with an opening formed in the distal end side of the insertion section and a suction section configured to suction an inside of the insertion channel from a suction port in communication with the insertion channel, the body fluid collection device comprising:
   a longitudinal member having a lumen formed along a longitudinal axis and configured to be inserted through the insertion channel;
   a flow path in which a suction is acted by the suction section of the endoscope, which is formed to bring the lumen of the longitudinal member in communication with the insertion channel in which the longitudinal member is inserted;
   an accommodating section which is formed in the flow path, and accumulate a body fluid suctioned in the lumen by the suction section of the endoscope; and
   a sealing member configured to seal a space between the longitudinal member inserted through the insertion channel and the inside of the insertion channel in a distal end side of the insertion channel so that a fluid does not flow from the distal end side to a proximal end side of the insertion channel, wherein:
      the flow path brings an opening of a proximal end side of the lumen in communication with an opening of the proximal end side of the insertion channel,
      a partition plate is provided at the flow path,
      the accommodating section is partitioned with the flow path by the partition plate,
      a first communication hole and a second communication hole penetrating in a plate thickness direction are formed in the partition plate,
      the longitudinal member is inserted through the second communication hole, and
      the opening of a proximal end portion of the lumen is disposed to be flush with a surface of an accommodating section side of the partition plate or disposed in the accommodating section.

2. The body fluid collection device according to claim 1 comprising:
   a filter provided at the flow path and configured to allow passing of a gas and not to allow passing of a liquid.

3. The body fluid collection device according to claim 1, wherein a filter configured to allow passing of a gas and not to allow passing of a liquid is provided at a hole formed in the flow path with no gap therebetween.

4. The body fluid collection device according to claim 1, wherein the accommodating section has a first accommodating section and a second accommodating section being disposed in parallel in a direction crossing the longitudinal axis in the proximal end portion of the longitudinal member with respect to the opening of the proximal end portion of the lumen and partitioned by a wall section,
   the wall section sides of the first accommodating section and the second accommodating section are opened, and the first accommodating section and the second accommodating section are in communication with each other.

5. The body fluid collection device according to claim 4, wherein a discharge hole is formed in the first accommodating section, and
   a plug member detachably attached to the discharge hole and which is capable of sealing the discharge hole is provided.

6. An endoscope system comprising:
   an endoscope having an insertion channel and a suction section configured to suction the inside of the insertion channel from a suction port in communication with the insertion channel; and
   the body fluid collection device according to claim 1.

7. An endoscope system comprising:
   an endoscope having an insertion channel and a suction section configured to suction the inside of the insertion channel from a suction port in communication with the insertion channel; and
   the body fluid collection device according to claim 2.

* * * * *